United States Patent [19]
Gerber et al.

[11] Patent Number: 5,641,519
[45] Date of Patent: Jun. 24, 1997

[54] METHOD OF TREATING ENDOTOXIC SHOCK EMPLOYING GALLIUM COMPOUNDS

[75] Inventors: Nicholas Gerber, Worthington; Glen Apseloff, Columbus; Daniel I. Mullet, Columbus; Mary Ellen Krecic, Columbus, all of Ohio

[73] Assignee: The Ohio State University, Columbus, Ohio

[21] Appl. No.: 444,211

[22] Filed: May 18, 1995

[51] Int. Cl.$^6$ .......................... A61K 33/24; A61K 31/28
[52] U.S. Cl. .............................. 424/650; 514/492
[58] Field of Search .......................... 514/492; 424/650

[56] References Cited

PUBLICATIONS

Embase Abstract No. 86042410 (Wilson) 1985.
Embase Abstract No. 89087280 (Schaiff et al.) 1989.
"Essentials of Nuclear Medicine Imaging", Third Edition, by Fred A. Mettler, Jr. and Milton J. Guiberteau, Published Dec. 4, 1990, Chap. 13, pp. 253–267.

*Primary Examiner*—Marianne M. Cintins
*Assistant Examiner*—M. Moezie
*Attorney, Agent, or Firm*—Fay, Sharpe, Beall, Fagan, Minnich & McKee

[57] ABSTRACT

A method of treating endotoxic shock in mammals, comprising administering an effective amount of a pharmaceutically acceptable gallium compound. A preferred gallium compound is gallium nitrate.

9 Claims, 1 Drawing Sheet

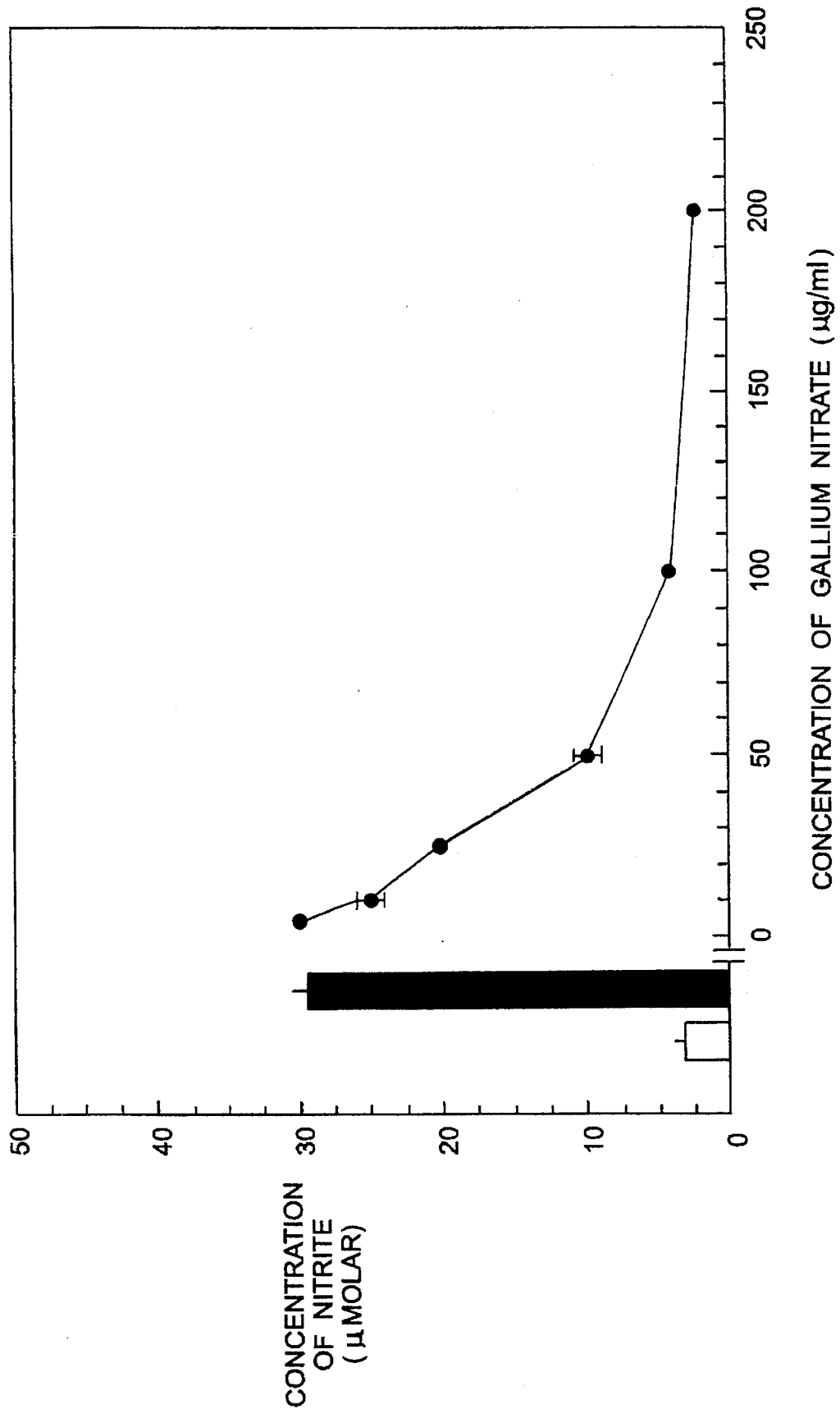

METHOD OF TREATING ENDOTOXIC SHOCK EMPLOYING GALLIUM COMPOUNDS

BACKGROUND OF THE INVENTION

This invention relates to a method of treating endotoxic shock. More particularly, this invention relates to methods of preventing the onset of endotoxic shock and alleviating endotoxic shock once it occurs.

The method of the present invention is particularly concerned with the administration of an effective amount of a pharmaceutically acceptable gallium compound to reduce the likelihood of endotoxic shock occurring in situations where endotoxic shock is frequently experienced, and the use of an effective amount of a pharmaceutically acceptable gallium compound to treat endotoxic shock after its onset.

Throughout the specification, numerous references will be made to use of gallium nitrate in the inventive method. However, it should be realized that the inventive method may be implemented with a variety of pharmaceutically acceptable gallium compounds.

DESCRIPTION OF THE ART

Endotoxic shock, for example septic shock, is a life-threatening condition which results from exposure to bacterial endotoxins. Particularly, bacterial lipopolysaccharides are a toxic moiety of the gram-negative bacteria outer membrane which is responsible for many of the pathophysiological events that occur during endotoxic shock. Although the body attempts to combat endotoxic shock by the release of cytokines, such as tumor necrosis factor (TNF), cardiovascular collapse frequently occurs. In fact, the particular process causing endotoxic shock related cardiovascular collapse is believed to be the release of vasoactive substances by the cytokines (ex. TNF).

More particularly, it is generally believed that the body's response in producing cytokines to combat the bacterial lipopolysaccharides coincidentally results in the production of nitric oxide, well known to cause a fall in blood pressure—the factor leading to death in most endotoxic shock fatalities.

Depression of the heart muscle activity occurs early on in endotoxic shock and coronary bloodflow is increased. However, circulation eventually becomes depressed and tissues suffer from a lack of oxygen causing the metabolic rate and energy requirements to increase. Accordingly, skeletal muscles may begin to break down in order to provide the body with protein as an energy source. Death eventually results from multiple organ failure or cardiac failure. A startling revelation is that the severe depression of body functions causes between 40 and 60% of patients who suffer from septic shock to die.

Typical treatments to combat endotoxic shock involve replacing lost fluids to support cardiac output and oxygen delivery throughout the body. Antibiotic therapy is also extremely important; however, this type of treatment is time-consuming and may not address the immediacy of the condition. Therefore, a number of drugs may also be given. In this regard, a great deal of research has been conducted on emergency treatments to reverse the effects of endotoxic shock on the cardiovascular system. For example, researchers have experienced limited success with NG-methyl-1-arginine and androgenous glucocorticoids as endotoxic shock treatment. Each of these treatments was selected to suppress nitric oxide production.

It has now been surprisingly found that gallium compounds, such as gallium nitrate, effectively suppress nitric oxide production and, therefore, can provide an effective treatment/prophylaxis for endotoxic shock. The discovery is surprising because gallium nitrate has been found to effectively treat arthritis; hypercalcemia; certain cancers; Paget's disease of bone; multiple sclerosis; and organ transplant rejections; however, there has been no suggestion in the art that gallium compounds are effective in the treatment of endotoxic shock.

SUMMARY OF THE INVENTION

Accordingly, it is a primary object of this invention to provide a new method of treating endotoxic shock.

It is an advantage of this invention to provide a new method of treating endotoxic shock which relies on a gallium compound recognized as pharmaceutically acceptable.

A still further advantage of this invention is the discovery that a pharmaceutically acceptable compound such as gallium nitrate can be utilized to reduce the likelihood of endotoxic shock onset and as a means of mitigating its effects once present in a patient.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the foregoing object and advantages in accordance with the purpose of the invention as embodied and broadly described herein, the treatment of this invention comprises administering an effective amount of a pharmaceutically acceptable gallium compound to a mammal. The inventive treatment can be utilized prophylactically in the case of a patient at high risk for the onset of endotoxic shock, such as those suffering from urinary or liver infections. Furthermore, the inventive treatment can be utilized to mitigate the effects of endotoxic shock once a patient is afflicted. It is believed that the treatment will be very effective in humans and horses, mammals particularly susceptible to endotoxic shock.

The treatment is preferably based on the use of an effective amount of a pharmaceutically accepted gallium compound selected from the group consisting of gallium nitrate, gallium citrate, gallium chloride, gallium carbonate, gallium acetate, gallium tartrate, gallium oxalate, gallium oxide, and hydrated gallium oxide. Within this group, gallium nitrate is a particularly preferred compound for the inventive treatment. Preferably, the gallium compound is administered topically, sublingually, perectum, orally, intravenously, subcutaneously, or intramuscularly.

BRIEF DESCRIPTION OF THE DRAWINGS

The invention consists in the novel parts, constitution, arrangement, combinations, and improvements shown and described. The accompanying drawing, which is incorporated in and constitutes a part of this specification, illustrates one embodiment of the invention and together with the description serves to explain the principles of the invention.

Of the drawings:

FIGURE 1 is a graphical depiction of the effect of gallium nitrate on nitrite production in LPS activated macrophage cells.

DETAILED DESCRIPTION OF THE INVENTION

Reference will now be made in detail to the present preferred embodiment of the invention, examples of which are illustrated in the following experiments. While the inventive process will be described in connection with the procedure, it will be understood that it is not intended to limit the invention to that procedure. On the contrary, it is intended to cover all alternatives, modifications, and equivalents as may be included within the spirit and scope of the invention defined by the appended claims.

Gallium is a metal that exhibits unique biochemical and clinical characteristics. For example, gallium acetate has been used extensively for the diagnostic localization of solid tumors which preferentially take up the radioactive tracer. Gallium nitrate has also been shown to inhibit the growth of solid tumors in animal models, and recently gallium has been approved by the Food and Drug Administration for the treatment of hypercalcemia of malignancy. As demonstrated in the following examples, intended to exemplify but not limit the invention, gallium compounds also effectively reduce the body's production of nitric oxide when bacterial lipopolysaccharides are present. Accordingly, gallium compounds are shown to be an effective drug for treatment of endotoxic shock.

EXAMPLES

The injection of *Proprionobacterium acnes* (*P. acnes*), lipopolysaccharide (LPS), and D-galactosamine (GaiN) is recognized to induce a macrophage-mediated hepatitis in male Balb/c mice that closely resembles human endotoxic shock. The article "Protective Effects of (2E)-3-[5-(2,3-Dimethoxy-6-Methyl-1,4-Benzoquinoyl)]-2-Nonyl-2-Propenoic Acid on Endotoxin-Mediated Hepatitis in Mice", from *The Journal of Pharmacology and Experimental Therapeutics*, Vol. 262, No. ©1992, fully describes this procedure.

In the present experiments, male Balb/c mice, 6–8 weeks old, were randomized into three groups and treated as follows: (1) saline, sodium citrate-injected controls; (2) hepatitis-induced, sodium citrate-injected controls; and, (3) hepatitis-induced, gallium-treated.

Macrophage-mediated hepatitis was induced in the mice of groups 2 and 3 by an intravenous injection of 0.3 mg/mouse *P.acnes* and one week later by the intravenous administration of 0.01 μg LPS/mouse and 10 mg GaiN/mouse. The mice of groups 2 and 3 were injected 24 hours before treatment with the LPS and Gain with 6.6 ml/kg sodium citrate solution and 45 ml/kg (6.6 ml/kg solution) elemental gallium (in the form of a nitrate), respectively.

The livers of each of the mice were evaluated histologically (microscopically) to determine the extent of inflammation and necrosis (cell death), and the blood was evaluated to measure standard liver function tests (SGOT, SGPT, GGT, and LDH). As will be understood by those skilled in the art, the gallium treated group 3 mice evidenced significantly lower biological markers associated with the induced hepatitis than group 2. 18 hours after inducing hepatitis, a portion of each group of mice were euthanized. As demonstrated in Table I, the mice treated with gallium (group 3) evidenced lowered serum aminotransferases, total bilirubin, and LDH levels versus animals treated with sodium citrate (group 2). This clearly evidences the effectiveness of gallium compounds in fighting endotoxic shock.

TABLE I

|  | Group 1 Control (N = 5) | Group 2 Hepatitis Control (N = 7) | Group 3 Hepatitis Gallium (N = 8) |
| --- | --- | --- | --- |
| Total Bilirubin | 0.1 ± 0.0 | 0.9 ± 0.37 | 0.2 ± 0.04 |
| GGT | 4.6 ± 2.6 | 8.0 ± 4.4 | 4.6 ± 1.9 |
| LDH | 784 ± 127 | 26133 ± 10414 | 3247 ± 1737 |
| SGOT | 99 ± 16 | 10986 ± 3062 | 1078 ± 549 |
| SGPT | 85 ± 28 | 17214 ± 4340 | 2088 ± 1097 |

18 hours after hepatitis was induced, blinded histological examination of the livers of groups 1, 2, and 3 was performed. The livers showed severe multifocal hepatitis and hepatic necrosis in the hepatitis-induced controls (group 2), whereas gallium-treated hepatitis-induced animals (group 3) showed only moderate hepatitis and minimal hepatic necrosis. There was no evidence of hepatitis or hepatocellular necrosis in the control animals (group 1).

To further investigate the ability of gallium compounds to mitigate nitric oxide related endotoxic shock, an in vitro system was established utilizing a murine bone marrow-derived macrophage cell line. The macrophage cell line was plated at a density of $10^6$ cells/ml and activated with 100 ng LPS/ml in culture to produce significant levels of nitrite (an indicator of nitric oxide production). The bars of FIGURE 1 demonstrate the effectiveness of the activation process as compared to cells not treated with LPS. The results of treating activated macrophages with gallium nitrate demonstrate a concentration-dependent inhibition of nitric oxide production. For comparison, sodium citrate and aluminum nitrate were added to LPS macrophage cells at equal molar concentrations; however, neither had an effect on the production of nitric oxide.

A cytokine believed to be involved in endotoxic-shock is tumor necrosis factor-α (TNF-α). TNF-α is the product of activated macrophages and therefore should be elevated in severe endotoxin-mediated diseases. Data indicated that TNF-α serum levels were elevated in our model of endotoxic shock; however, gallium treatment did not lower the TNF-α serum levels significantly.

This evidence suggests (in combination with the in vitro studies of endotoxic shock) that gallium selectively inhibits the production of nitric oxide without affecting the production of TNF-α. Therefore, gallium can provide protection against severe endotoxin-mediated diseases by selectively inhibiting the production of nitric oxide by activated macrophages. These findings suggest that gallium can attenuate endotoxin-mediated diseases by selectively inhibiting the production of nitric oxide and, therefore, may be efficacious in endotoxin-mediated shock in humans and other mammals.

Thus, it is apparent that there has been provided, in accordance with the invention, a method for treating endotoxic shock that fully satisfies the objects, aims, and advantages set forth above. While the invention has been described in conjunction with the specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A method of treating endotoxic shock in humans, comprising administering an effective amount of a pharmaceutically acceptable elemental gallium compound to a human suffering from endotoxic shock.

2. The method of claim 1 wherein said gallium compound is selected from the group consisting of gallium nitrate, gallium citrate, gallium chloride, gallium carbonate, gallium acetate, gallium tartrate, gallium oxalate, gallium oxide, and hydrated gallium oxide.

3. The method of claim 2 wherein said gallium compound is gallium nitrate.

4. The method of claim 1 wherein said gallium compound is administered topically, sublingually, perectum, orally, intravenously, subcutaneously, or intramuscularly.

5. The method of claim 1 wherein said endotoxic shock is at least partially caused by a bacteria.

6. A method of treating endotoxic shock in animals comprising administering an effective amount of a pharmaceutically acceptable elemental gallium compound to an animal suffering from endotoxic shock.

7. The method of claim 6 wherein said animal is a horse.

8. The method of claim 6 wherein said gallium compound is selected from the group consisting of gallium nitrate, gallium citrate, gallium chloride, gallium carbonate, gallium acetate, gallium tartrate, gallium oxalate, gallium oxide, and hydrated gallium oxide.

9. The method of claim 6 wherein said gallium compound is gallium nitrate.

* * * * *